United States Patent
Antaki et al.

[11] Patent Number: 6,066,086
[45] Date of Patent: May 23, 2000

[54] SPEED CONTROL SYSTEM FOR IMPLANTED BLOOD PUMPS

[75] Inventors: James F. Antaki, Allison Park; Seongjin Choi, Pittsburgh; John Robert Boston, Wexford, all of Pa.; Kenneth C. Butler; Douglas C. Thomas, both of Carmichael, Calif.; Devin V. Amin, Rancho Cordova, Calif.

[73] Assignee: Nimbus, Inc., Rancho Cordova, Calif.

[21] Appl. No.: 09/034,674

[22] Filed: Mar. 4, 1998

Related U.S. Application Data

[63] Continuation-in-part of application No. 08/740,749, Nov. 1, 1996, Pat. No. 5,888,242.

[51] Int. Cl.[7] .............................. A61N 1/362; A61M 1/00
[52] U.S. Cl. .................................................. 600/17; 623/3
[58] Field of Search ................................... 623/3; 604/66, 604/67, 50, 13, 65, 92, 19, 1.8, 151, 246, 503, 505; 417/1; 415/206; 607/25–26; 600/16–17

[56] References Cited

U.S. PATENT DOCUMENTS

| | | | |
|---|---|---|---|
| 3,985,123 | 10/1976 | Herzlinger et al. | 600/17 |
| 4,809,681 | 3/1989 | Kantrowitz et al. | 600/17 |
| 5,693,091 | 12/1997 | Larson, Jr. et al. | 623/3 |
| 5,697,884 | 12/1997 | Francischelli et al. | 600/17 |
| 5,722,930 | 3/1998 | Larson, Jr. et al. | 600/16 |
| 5,807,234 | 9/1998 | Bui et al. | 600/17 |
| 5,833,619 | 11/1998 | Freed et al. | 600/485 |
| 5,888,242 | 3/1999 | Antaki et al. | 623/3 |

*Primary Examiner*—Sharon Finkel
*Attorney, Agent, or Firm*—Harry G. Weissenberger

[57] ABSTRACT

An automatic speed control system continually adjusts the speed of an implanted cardiac assist blood pump to an optimum level for the varying physiological needs of the patient. It does this by periodically iteratively incrementing the speed setpoint of the pump. When the system detects the imminence of a ventricular collapse at diastole, it decrements the speed setpoint by a predetermined safety margin. An alarm condition is provided if the setpoint decrease results in an insufficient blood flow rate through the pump. The flow rate and imminence of ventricular collapse are computed in real time as functions of only the pump's motor current and speed setpoint.

4 Claims, 8 Drawing Sheets

SPEED CONTROL SYSTEM FOR IMPLANTED BLOOD PUMPS

RELATED CASES

This case is a continuation-in-part of application Serial No. 08/740,749 filed Nov. 1, 1996, now U.S. Pat. No. 5,888,242.

FIELD OF THE INVENTION

The present invention relates to implanted blood pump systems, and more particularly to an adaptive speed control for continuously driven blood pumps so as to automatically regulate the speed of the pump in accordance with the physiological needs of the patient.

BACKGROUND OF THE INVENTION

Implantable blood pumps for chronic left ventricular assist have been and are being developed in a number of forms. For example, an implantable, transcutaneously powered electric axial flow pump is shown in U.S. Pat. No. 5,588,812 entitled Implantable Electric Axial-Flow Blood Pump. Inasmuch as the blood flow requirements of the human body vary substantially and unpredictably with posture, stress, activity, ambient temperature and other physiological and psychological factors, it is necessary to continually adapt the pump's flow rate to the patient's needs.

Two factors limit the usable speed range of, e.g., the axial flow pump of U.S. Pat. No. 5,588,812. At the lower end, the speed must be sufficient to produce enough blood flow to deliver essential substances to the vital issues and remove products of metabolism, as well as cool the bearings and prevent thrombus formation. At the upper end, the pump speed must not be so high as to produce a zero or negative pressure within the inlet during diastole (i.e. it must never cause suction in the ventricle). The pump is most effective when operating close to the upper end of the range.

In an ambulatory patient, it is not always practical to directly measure the pressure and flow rate information necessary for pump control, because the necessary sensors would complicate the pump's electronics and present unnecessary failure risks.

It has previously been hypothesized, as pointed out in the article entitled "In Search of Chronic Speed Control for Rotary Blood Pumps" in the Proceedings of the Waseda International Congress of Modeling and Simulation Technology for Artificial Organs in Tokyo, Japan on Aug. 1–3, 1996, that the pump motor current, voltage and speed may contain information from which pressures and flow rates may be determined. However, no practical way of evaluating that information in real time and putting it to use in a physiological environment has been determined to date.

SUMMARY OF THE INVENTION

The invention provides an automatic, physiologically driven speed control for an implanted rotary or other continuously driven electric blood pump which continually adjusts the pump speed in real time to produce an optimum blood flow rate through a wide range of short-term and long-term changes in the patient's physiology, using only the current and speed of the pump motor as measured control parameters.

Basically, the system of this invention consists of a brushless, electronically commutated DC motor whose rotor is part of the pump rotor, and whose speed is conventionally controlled, in accordance with a setpoint signal provided by a microprocessor, by a switching network responsive to the motor's back electromagnetic force (BEMF). The microprocessor periodically increments that setpoint signal iteratively until it detects the imminence of a ventricular collapse, and then decrements the setpoint signal slightly. Consequently, the pump always operates at the optimum speed for the patient's physiological requirements at any given time i.e. at the limit of venous return (the imminence of suction). In more formal terms of optimal control theory, this operation can be expressed as minimize {atrial pressure} subject to:

atrial pressure > threshold − 1(approx. + )

arterial pressure > threshold − 2 flow > theshold − 3 wherein "ventricular diastolic pressure" could be substituted for "atrial pressure" if desired, and wherein threshold-2 is a function of flow.

The detection of an imminent ventricular collapse (i.e. ventricular suction at diastole) can be done in several ways by monitoring the pump motor current draw. In a first embodiment of the invention, the cyclical current fluctuations during the systole-diastole cycle are monitored. It has been empirically determined that a detectable current spike occurs just prior to a ventricular collapse caused by suction. Consequently, the detection of this current spike can be used to reduce the pump speed to a safe value.

In another embodiment of the invention, advantage is taken of the fact that the mean flow rate increases at an incrementally decreasing rate as pump speed is increased. Consequently, the derivative of the flow rate (in accordance with the invention, the flow rate can be calculated in real time from the motor current) with respect to speed (i.e. the setpoint signal) can be used as a speed reduction signal when the derivative drops below a predetermined minimum.

In a third embodiment of the invention, it has been found that the second harmonic of the current fluctuation during a heartbeat cycle increases substantially shortly before ventricular collapse occurs. Thus, a spectral analysis representation of the time-current wave form during the heartbeat cycle can be continuously computed, and a speed reduction signal can be generated when the second harmonic term of the series exceeds a predetermined threshold.

Finally, a fourth embodiment of the invention is based on the recognition that a monitoring of the opening and closing of the aortic and mitral valves provides accurate information on the imminence of ventricular collapse. This monitoring can be done by detecting valve sounds with an implanted microphone or hydrophone, but in keeping with the invention, it may also be done electronically by measuring the pulsatility of the motor current. In either mode, motor speed is adjusted so that the aortic valve does not open on every heartbeat cycle but that the mitral valve closes on every cycle.

On the other end of the operational range, an alarm signal can be generated when the flow rate drops below a preset minimum necessary for the safe operation of the pump. As pointed out above, the flow rate can be continually calculated in real time in accordance with the invention, knowing the motor current and speed setpoint.

By the use of the invention, the pump speed can be continually adjusted to an optimal level not only in response to transient changes in the patient's physiology, but also in response to long-term changes such as the patient's recovery from heart disease.

DESCRIPTION OF THE PREFERRED EMBODIMENT

Figure 1:
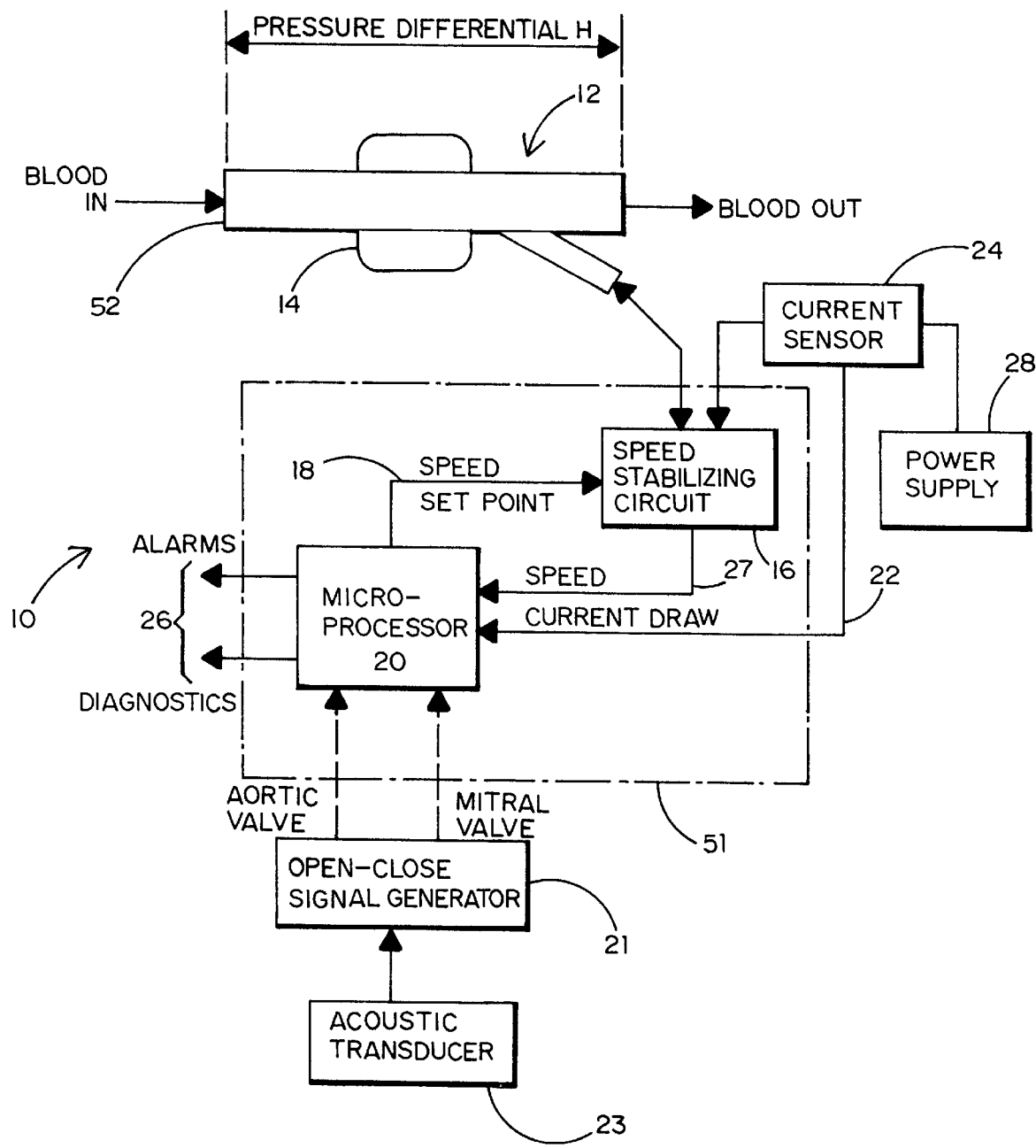
FIG. 1 is a block diagram illustrating the inventive system.
Figure 2:
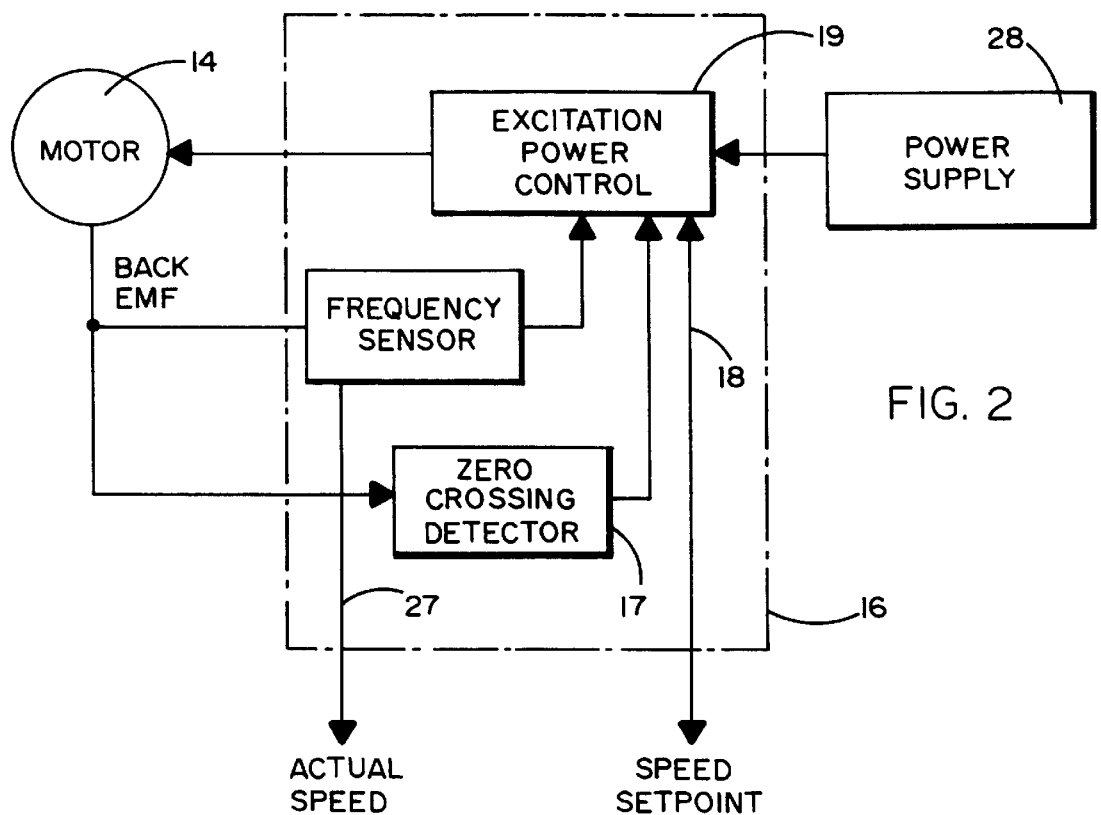
FIG. 2 is a block diagram of the speed stabilizing circuit.

FIG. 1 shows the system 10 to include an implanted axial flow blood pump. 12 (the principles of this invention are equally applicable to other types of blood pumps such as centrifugal pumps) driven by a brushless DC motor 14. The speed of the motor is maintained, by a speed stabilizing circuit 16, at a level dictated by the setpoint signal 18. The speed stabilizing circuit 16 (FIG. 2) is microprocessor based and is responsive to the back electromotive force (BEMF) generated by the motor. A zero crossing detector 17 detects the zero crossings of the BEMF curve and applies an indication thereof to the excitation power control 19. The control 19 uses the BEMF and the timing of the zero crossing of the BEMF as control parameters to adjust the motor excitation power. The speed stabilizing microprocessor 16 can be integrated with the speed control microprocessor 20 into a single microprocessor 51 (FIG. 1).

The setpoint signal 18 is produced by a microprocessor 20 whose sole input variable is the motor current draw signal 22 produced by current sensor 24 having power supply 28. Alternatively, the input to microprocessor 20 can be acoustically generated signals representing the opening and closing of the aortic and mitral valves of the patient's heart in the sensing method of FIG. 13. These signals can be conventionally generated by an open-close signal generator 21 in response to audio inputs from an implanted acoustic transducer 23. The microprocessor 20 may conveniently have alarm and diagnostic outputs 26 through which the operation of the system can be observed, and alarm indications or remedial action such as defibrillation can be initiated. The operation of the microprocessor 20 is described in more detail below.

Two parameters are known to the microprocessor 20 without the use of any sensors: a) the pump speed ω (speed signal 27); and b) the current I (current signal 22) drawn by the motor 14.

The dynamics of a three-winding brushless DC motor such as the motor 14 can be described as $$Jd\omega/dt = T_e - B\omega - T_p \qquad (1)$$

and $$T_e = K_B \sin(\theta)i_a + K_B \sin(\theta - 2\pi/3)i_b + K_B \sin(\theta - 2\pi/3)i_c \qquad (2)$$

wherein $i_a$, $i_b$ and $i_c$ are the phase currents in the three windings, ω is the rotor speed, θ is the angular position of the rotor, J is the inertia of the rotor, B is the damping coefficient, $K_B$ is the back EMF constant, $T_e$ is the motor torque, and $T_p$ is the load torque on the pump 12.

Because the motor 14 has a sinusoidal back EMF, the phase currents also have a sinusoidal wave form. Consequently, the motor torque $T_e$ can be expressed simply as $$T_e = 3/2 K_B I \qquad (3)$$

wherein I is the sum of the phase currents. Applying formula (3) to formula (1), we find that $$Jd\omega/dt = 3/2 K_B I - B\omega - T_p \qquad (4)$$

The load torque $T_p$ is in turn expressible as $$T_p = a_o \omega^3 + a_1 Q \omega^2 \qquad (5)$$

in which $a_o$ and $a_1$ are empirically determined coefficients for a given pump 12, and Q is the blood flow rate through the pump 12. Combining equations (4) and (5), we find that $$Jd\omega/dt = 3/2 K_B I - B\omega - (a_o \omega^3 + a_1 Q \omega^2) \qquad (6)$$

The terms of equation (6) can now be transposed to solve for Q as a function of I and ω:

$$Q = \frac{\frac{3}{2}K_B I - B\omega - \left(a_0 \omega^3 + J\frac{d\omega}{dt}\right)}{a_1 \omega^2} \qquad (7)$$

in which J, $K_B$, B, $a_o$ and $a_1$ are all constants for a given pump motor 14; ω is represented by the speed signal 18 of FIG. 1, i.e. an input of microprocessor 20; and I is the only measured variable input applied to the microprocessor 20.

One of the limit parameters of the pump 12 is the minimum blood flow Q which the pump 12 can sustain without risking mechanical and/or physiological damage. Consequently, if a decrease in the speed setpoint signal 18 causes Q to drop to, e.g., 5 l/min., the microprocessor must not reduce the speed setpoint any further, and an alarm condition is present.

The other limit parameter for the pump 12 is the avoidance of left ventricular suction, i.e. the avoidance of any condition in which the pressure at the inlet 52 of the pump 12 (or, more accurately, the pressure at the tip of the inlet cannula of the pump 12 which protrudes into the left ventricle) goes negative at diastole. Inasmuch as that pressure is not known without a sensor, the microprocessor 20 must determine the imminence of such a condition internally or from the current input 22 alone.

Because it is physiologically desirable to operate the pump 12 at a level at which the inlet pressure at diastole is slightly above zero, the microprocessor 20 is programmed to continually, e.g. every ten seconds or so, or perhaps after each twelfth or so heartbeat (heartbeats can be identified by the cyclical variations of I between systole and diastole), increase the speed setpoint and look for signs of imminent ventricular collapse (i.e. ventricular suction), then reduce the setpoint slightly. In that manner, the microprocessor 20 can continually adjust the pump speed in real time to its optimum level for the patient's varying physiological demands.

Figure 3:
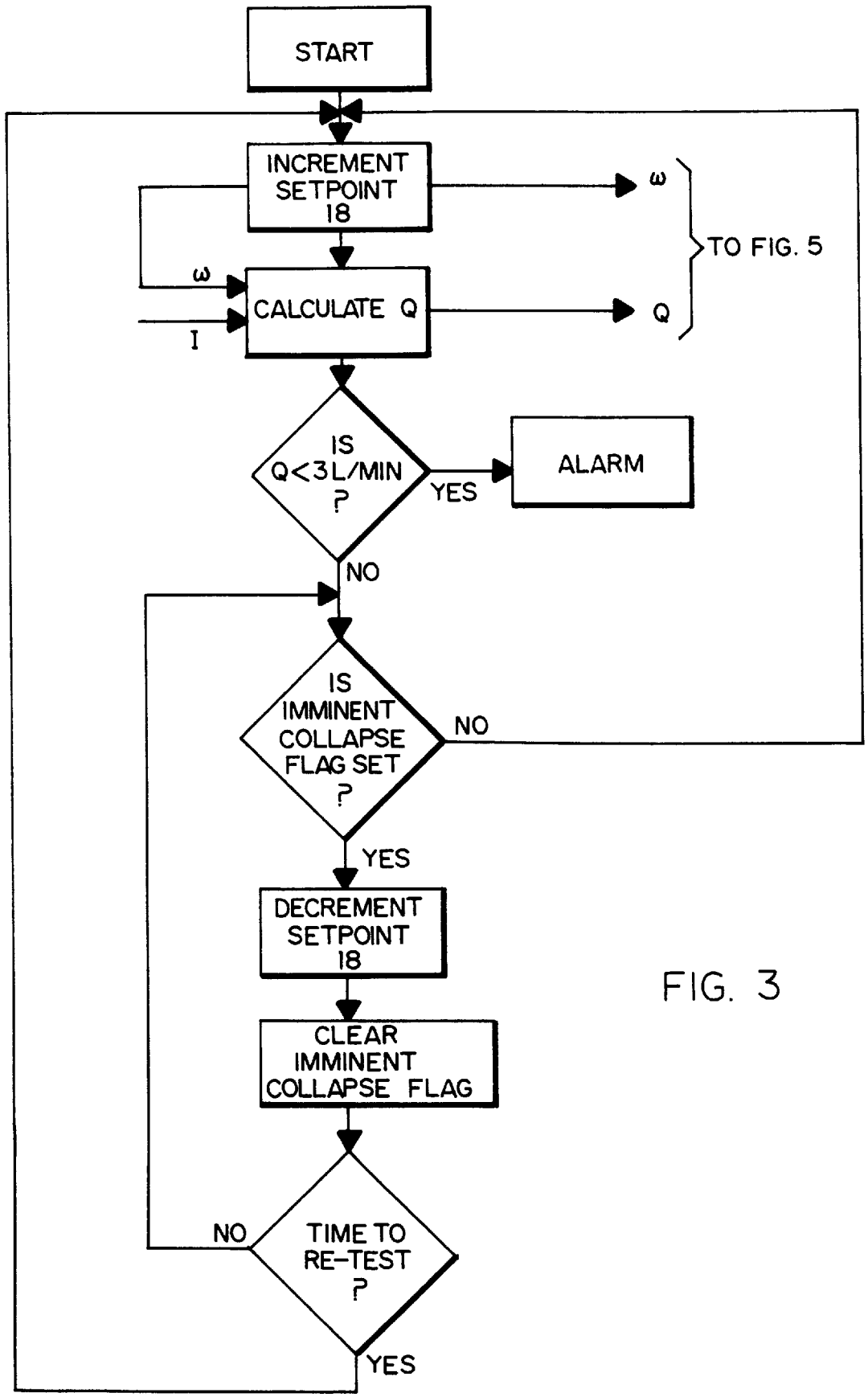
FIG. 3 is a flow chart of the control microprocessor's main routine.

FIG. 3 depicts, in flow chart form, the foregoing mode of operation of microprocessor 20. As shown in that figure, the microprocessor periodically, at the appropriate time intervals mentioned above, computes the blood flow rate Q and tests the maximum speed at which the pump 12 can be operated without causing ventricular collapse. It looks continuously, however, for signs of imminent ventricular collapse, so that if one occurs between computation cycles, the pump speed will immediately be decremented to a safe value.

Inasmuch as provisions can be made in the microprocessor 20 to vary the test time interval and the amount of decrementation following the detection of an imminent ventricular collapse, the system of this invention can be made to allow the cardiologist to gradually wean the patient's heart from the blood pump 12 as the heart's health improves. For this purpose, the decrementation and test interval can be increased (as long as the decrementation is not so large as to cause the insufficient flow alarm condition) so as to make the heart operate at a higher pressure for longer intervals.

Figure 4:
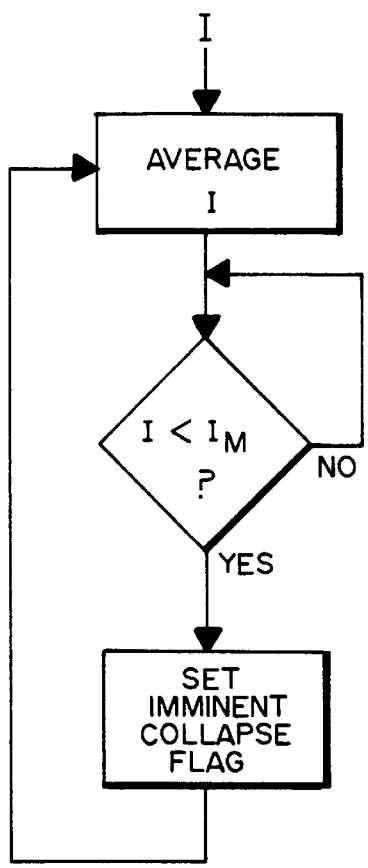
FIG. 4 is a flow chart illustrating two embodiments of an imminent ventricular collapse flagging routine.

The detection of imminent ventricular collapse can be done in a variety of ways exemplified by the four preferred embodiments of the invention. In the first embodiment (FIG. 4), advantage is taken of the fact that the motor current I normally tracks the flow rate Q quite consistently, but spikes noticeably in the negative direction at diastole when the inflow pressure approaches zero, i.e. when the outflow demand starts to exceed inflow supply. Consequently, the detection in the first embodiment is done by averaging the motor current and setting an imminent collapse flag when the flow (and hence the current) momentarily drops below that average by more than a predetermined adaptive threshold amount $I_M$.

Figure 5:
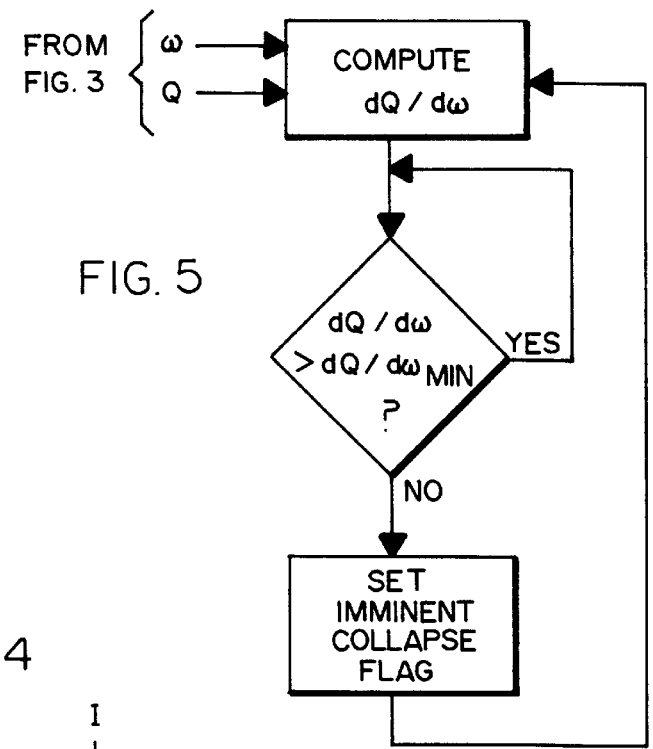
FIG. 5 is a flow chart illustrating a third embodiment of an imminent ventricular collapse flagging routine.

In a second embodiment of the invention (FIG. 5), advantage is taken of the fact that with increasing pump speed, the mean blood flow rate through the pump 12 should increase at an incrementally decreasing rate. When the patient's venous return is matched by the pump 12, this rate becomes zero. Because ventricular suction may occur prior to that point, an empirically determined minimum rate of flow increase with speed increase is advantageously set to trigger the flag; in other words, the flag is set when $dQ/\omega < dQ/d\omega_{MIN}$.

Figure 6:
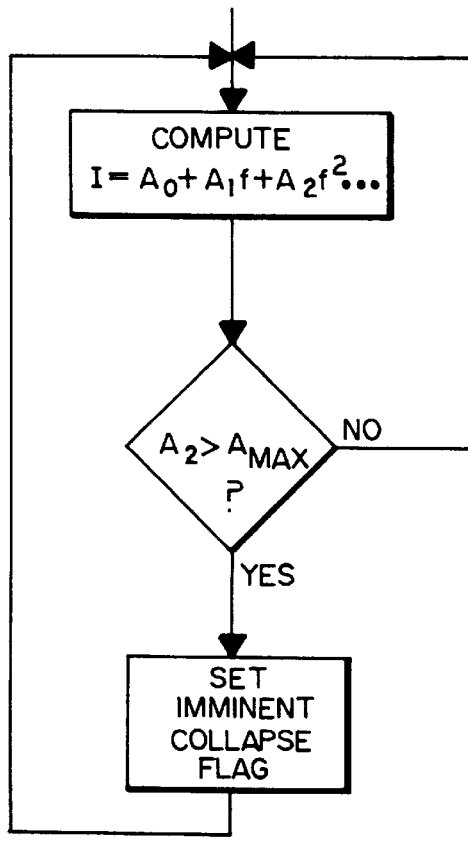
FIG. 6 is a flow chart illustrating a fourth embodiment of an imminent ventricular collapse flagging routine.

In the third embodiment of the invention (FIG. 6), advantage is taken of the empirically discovered fact that the second harmonic component of the motor current waveform rises substantially as the pump speed approaches the ventricular collapse danger point. Consequently, another way of detecting imminent collapse is to compute a spectral analysis of the motor current I with the heartbeat frequency f as the fundamental frequency, and to trigger the imminent collapse flag when the second harmonic coefficient $A_2$ exceeds a predetermined value $A_{MAX}$.

FIGS. 7–10 illustrate another approach for determining the target control zone. The method of FIGS. 7–10 is based on the fact that left ventricular assist devices using atrial or ventricular cannulation establish a pathway parallel to the native left ventricle for blood flow from the pulmonary to the systemic vasculature. Thus, axial flow ventricular assist devices (VADs) add new hemodynamic states to the normal physiology. These new states are a decreased pulse pressure, and more notably the possibility of the aortic valve remaining closed at all points during the cardiac cycle. Axial flow pumps, unlike passively filling pulsatile VADs, have the capacity to develop negative inflow pressures at all points during the cardiac cycle which can preclude the opening of the aortic valve. Aortic valve status therefore becomes one of the critical parameters to be controlled while using an axial flow VAD.

Figure 7:
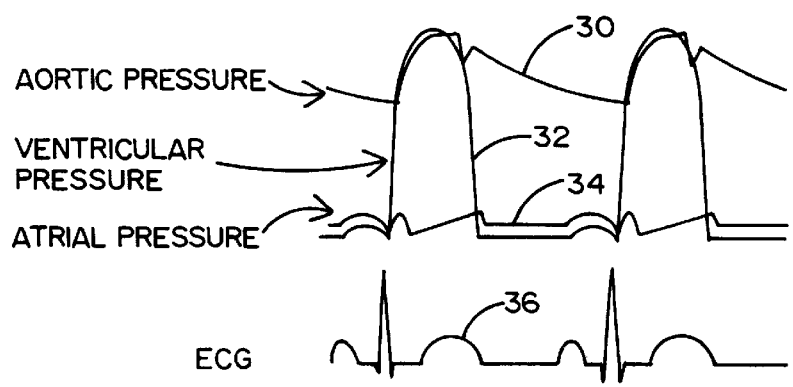
FIG. 7 is a time-amplitude diagram illustrating the normal interrelationship of aortic, ventricular and atrial pressure during the heartbeat cycle.
Figure 8:
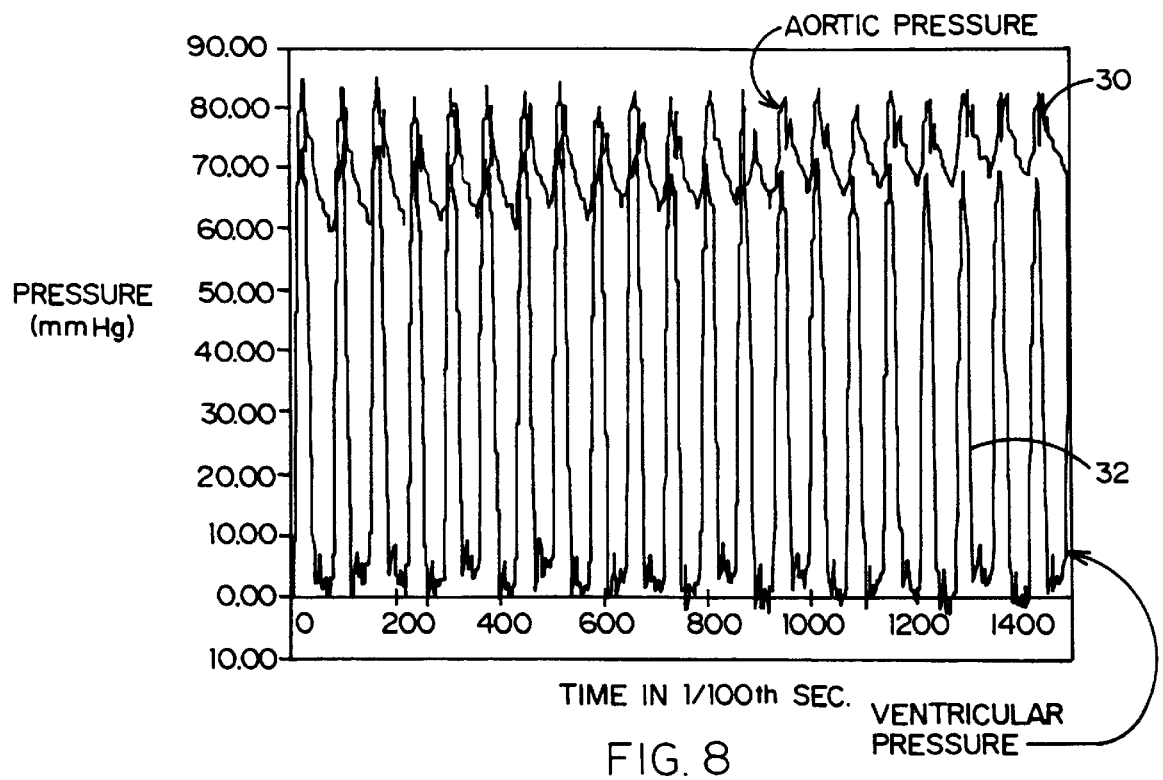
FIG. 8 is a time-amplitude diagram illustrating normal aortic and ventricular pressure cycles.
Figure 9:
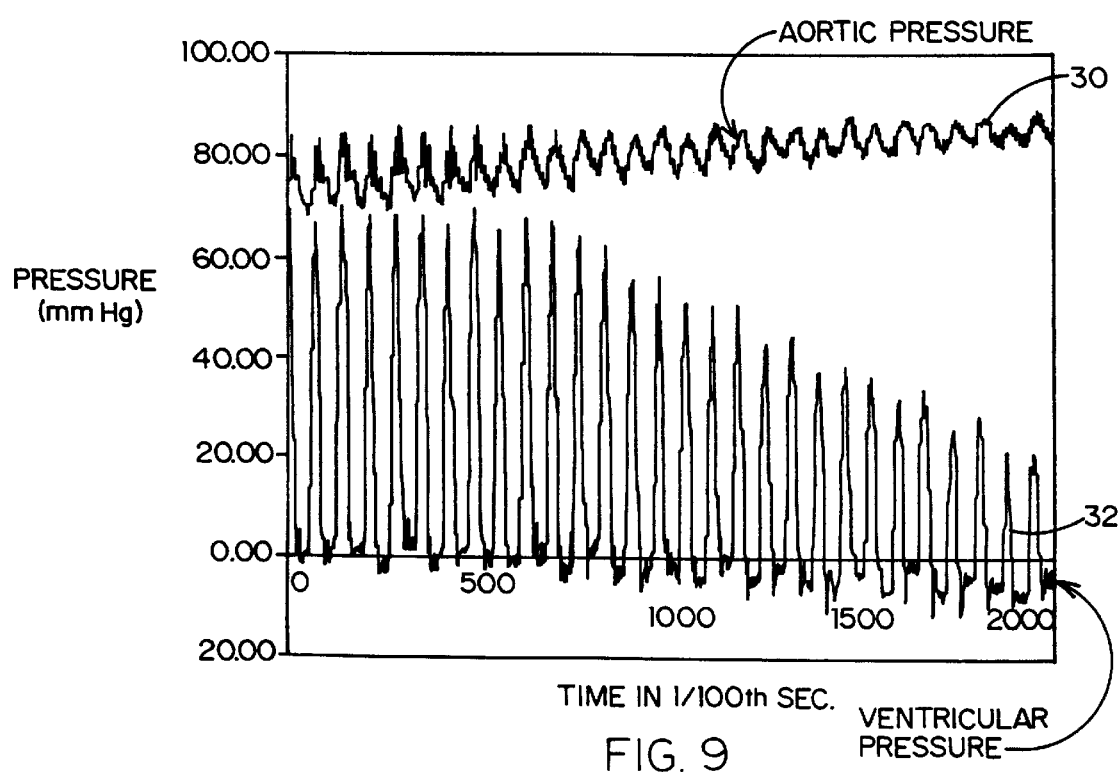
FIG. 9 is a diagram similar to FIG. 8 but showing the change in the pressure cycles when an axial flow blood pump is used with increasing speed.

FIG. 7 shows the normal aortic and ventricular pressure wave shapes 30 and 32, respectively, as well as the normal atrial pressure 34, as related to the ECG trace 36. FIG. 8 shows the wave shapes 30 and 32 when an axial flow VAD is operating with increasing output. It shows an aortic pressure which is elevated due to the pump support as well as a diminishing pressure variation, or pulsatility, per heart cycle as the pump output increases. Once the VAD output exceeds the venous return, the aortic valve remains closed because the ventricular pressures 32 never exceed the aortic pressure 30. At this point all systemic circulation is supplied by the VAD and the native ventricle is in a state of marked unloading. Further unloading will result in additional reduction of the inlet pressure and may cause the mitral valve to remain open during systole, resulting in a significant risk of ventricular collapse. FIG. 9 illustrates the continued reduction in ventricular pressure with increasing pump output. This physiology also underlies the method of FIG. 5 described above.

Figure 10:
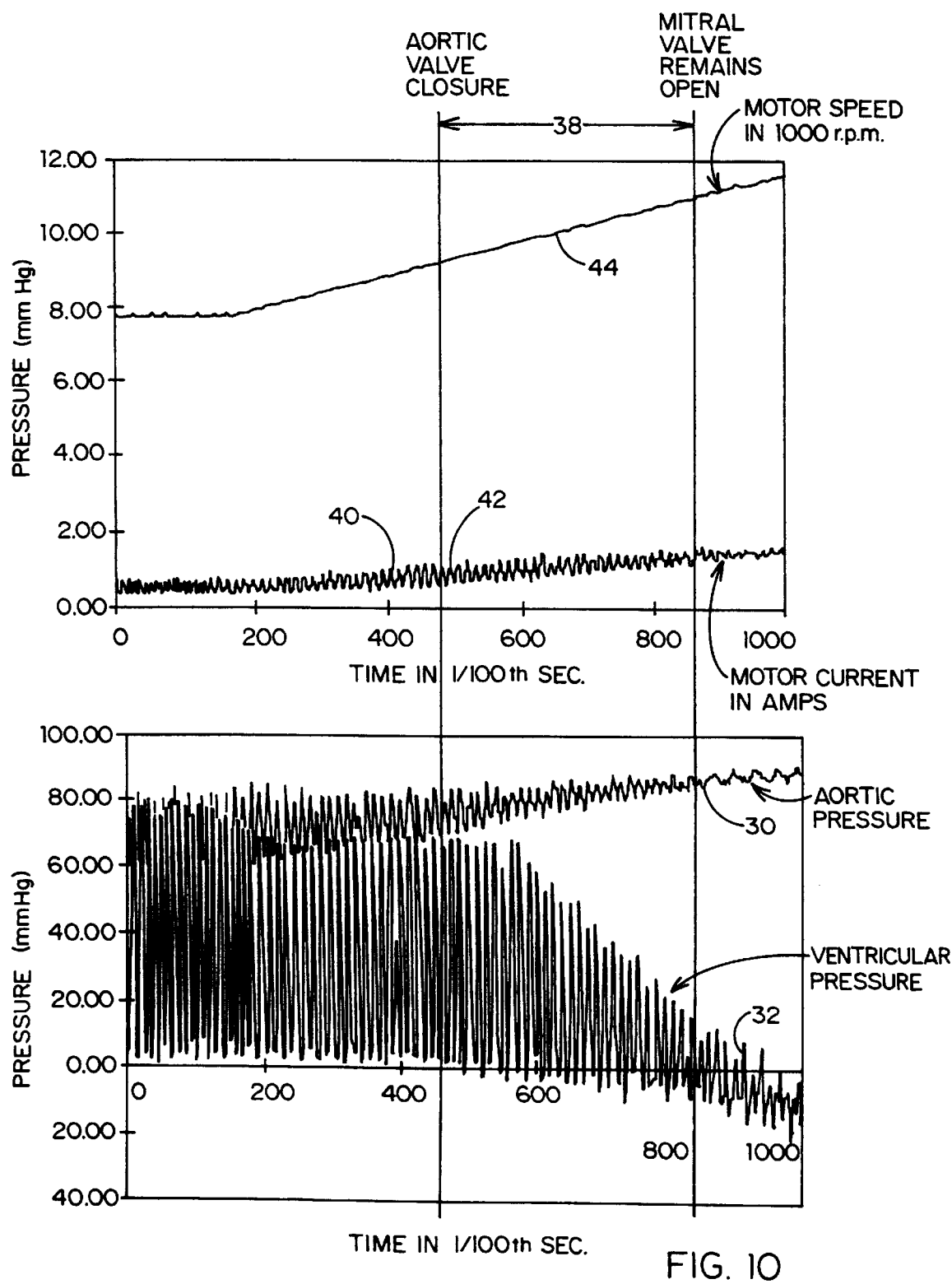
FIG. 10 is a set of time-amplitude diagrams showing the correlation of blood pump motor speed and motor current with aortic and ventricular pressure cycles in the target control zone.

The present invention provides a speed control algorithm based on the state of the aortic and mitral valves. The purpose of this algorithm, like that of the other algorithms described above, is to regulate pump speed so that maximum ventricular relief is provided while preventing the pump from generating negative ventricular pressure which can collapse the ventricle. The target control zone 38 is shown in FIG. 10. By adjusting pump speed so that the aortic valve remains closed on most cycles while the mitral valve closes on every cycle, maximum relief is provided while avoiding ventricular collapse.

One approach for detecting the opening and closing of the valves in accordance with this invention would be to use an acoustic transducer 23 (FIG. 1) such as an implanted microphone or hydrophone to detect the valve sounds. However, such implantation can be avoided by monitoring the motor current 40 for a diminished pulsatility. While the aortic valve is opening, a change of pressure occurs across the pump. This change in pressure results in a changing flow which in turn is reflected by the motor current. At the point 42 that the aortic valve stays closed, there is a decrease in the pulsatility. Further unloading by the pump decreases the ventricular filling, further decreasing the pulsatility. The amount of ventricular relief can therefore be determined by the pulsatility (i.e. the peak-to-peak spread) of the current. The speed is regulated to maintain a specific amount of pulsatility, thus avoiding the region of ventricular collapse. It may be desirable to cause the control to periodically operate in that region so as to maintain aortic valve function as prolonged periods of valve closure may be undesirable.

Figure 11:
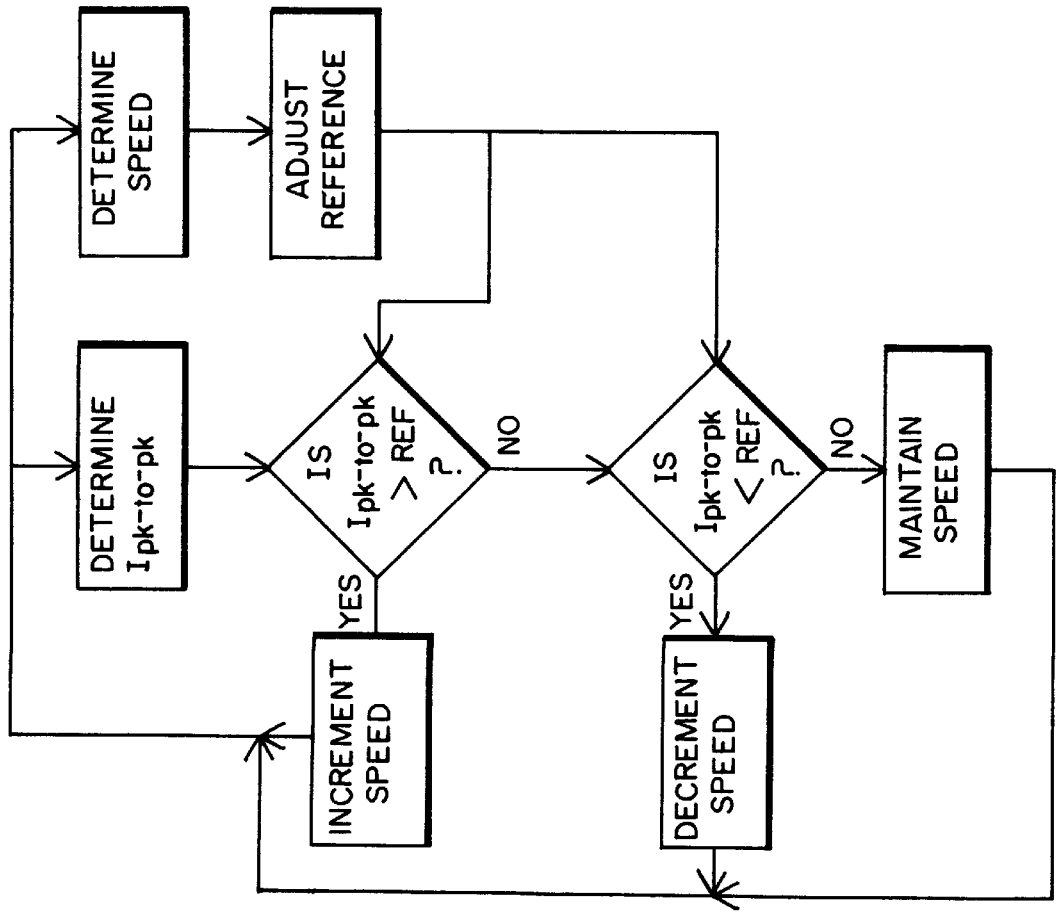
FIG. 11 is a flow chart illustrating the pulsatility-measuring method of speed control.

The foregoing physiology can be translated into an operational algorithm for the microprocessor 20 as follows (see FIG. 11):

1) Monitor motor current over a 2 second interval;
2) Determine the maximum and minimum current value over this interval;
3) If the difference between the minimum and the maximum is larger than the reference increase speed. If the difference between the minimum and maximum is less than the reference decrease speed, else maintain speed constant;
4) Sample another interval of motor current.

It should be noted that the reference value used in this algorithm is speed-dependent, i.e. it varies with changes in pump speed. Appropriate reference values are determinable empirically and by modeling the pump motor and cardiac system.

Figure 12:
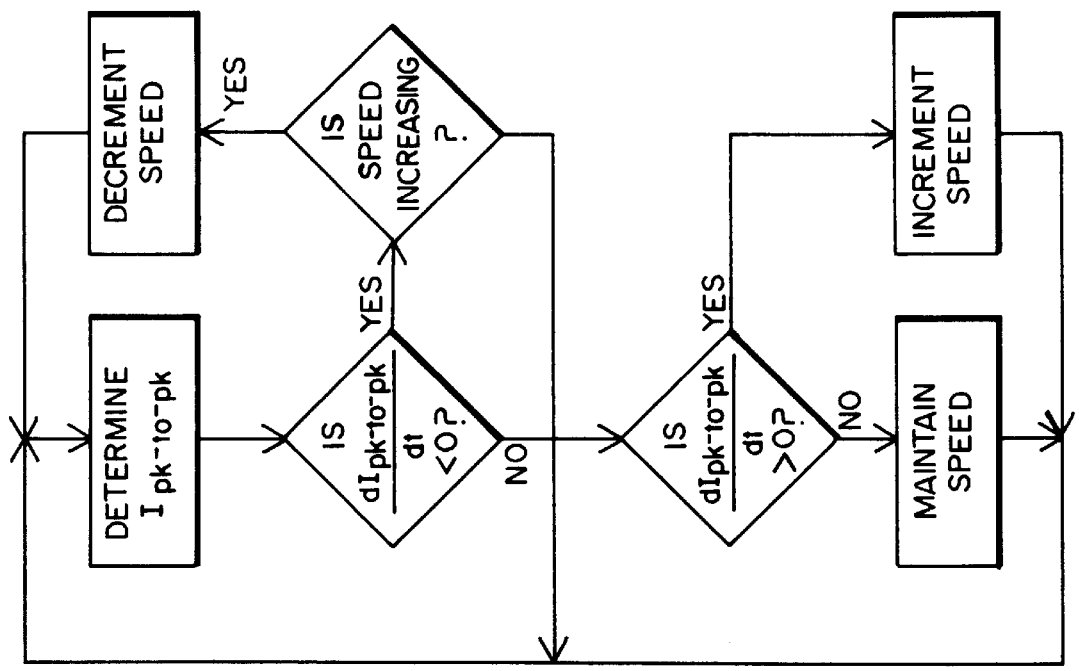
FIG. 12 is a flow chart illustrating the speed control method using the slope of the peak-to-peak current with increasing speed.

An alternate approach is to look for a reduction in the peak-to-peak current pulse with increasing speed (see FIG. 12). This approach is similar to the diminishing flow algorithm described above, except it does not require the calculation of flow and does not require a reference value because the current value is compared to a previous value.

Figure 13:
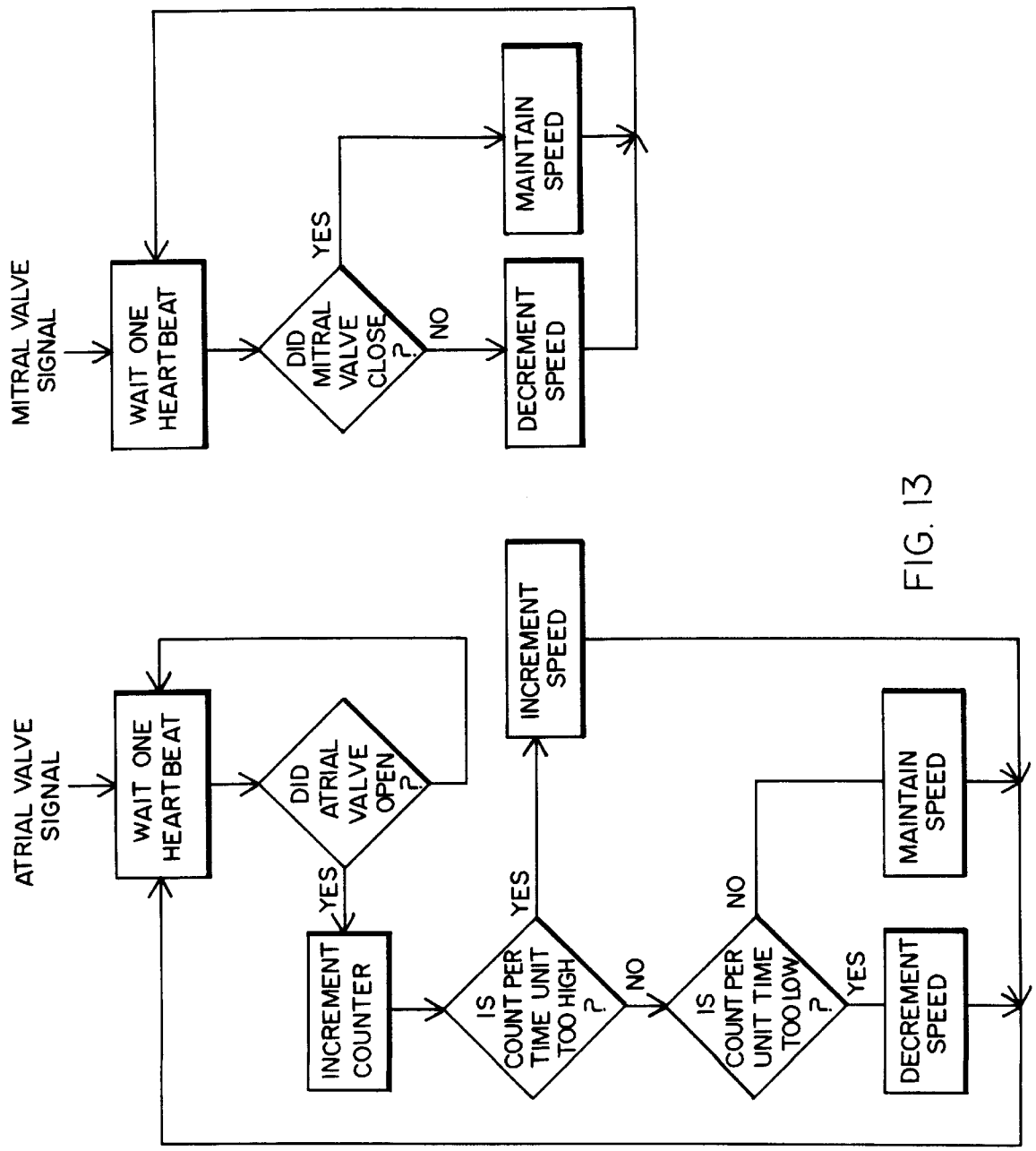
FIG. 13 is a flow chart of the acoustically driven speed control method.

The acoustic sensing of the impending ventrical collapse by monitoring the aortic and mitral valve action can be carried out as illustrated in FIG. 13. The characteristic sounds of the aortic and mitral valves opening and closing can be used by a signal generator 21 (FIG. 1) to provide "open" and "closed" signals to the microprocessor 20. The microprocessor 20 can derive motor control information from these signals as shown in FIG. 13.

It should be understood that the exemplary speed control system for implanted blood pumps described herein and shown in the drawings represents only a presently preferred embodiment of the invention. Indeed, various modifications and additions may be made to such embodiment without departing from the spirit and scope of the invention. Thus, other modifications and additions may be obvious to those skilled in the art and may be implemented to adapt the present invention for use in a variety of different applications.

We claim:

1. A method of automatically controlling the speed of an axial flow ventricular assist device, in accordance with a patient's time-varying physiological requirements, comprising the steps of:
   a) sensing the opening and closing of the aortic and mitral valves of the patient's heart; and
   b) maintaining said speed at a level where the aortic valve remains closed on most cycles of the patient's heartbeat to avoid ventricular collapse, and the mitral valve opens and closes on every cycle.

2. The method of claim 1, in which said sensing step includes:
   i) measuring the pulsatility of the motor current of said device; and
   ii) determining the speed at which said pulsatility decreases to a predetermined reference value.

3. The method of claim 1, in which said sensing step includes:
   i) continually determining the average peak-to-peak value of the motor current of said device over a period of several cycles;
   ii) incrementally increasing motor speed if said average peak-to-peak value is above a predetermined reference value; and
   iii) incrementally decreasing motor speed if said average peak-to-peak value is below said predetermined reference value.

4. The method of claim 1, in which said sensing step is performed acoustically by detecting heart sounds.

* * * * *

UNITED STATES PATENT AND TRADEMARK OFFICE
CERTIFICATE OF CORRECTION

| | |
|---|---|
| PATENT NO. | : 6,066,086 |
| APPLICATION NO. | : 09/034674 |
| DATED | : May 23, 2000 |
| INVENTOR(S) | : Devin V. Amin et al. |

Page 1 of 1

It is certified that error appears in the above-identified patent and that said Letters Patent is hereby corrected as shown below:

At Column 1, immediately following the first full paragraph, please insert the following paragraph:

--STATEMENT AS TO FEDERALLY SPONSORED RESEARCH
Funding for the work described herein was provided in part by the National Institutes of Health, Grant No. NO1-HV-58155. The federal government may have certain rights in the invention.--

Signed and Sealed this

Twentieth Day of February, 2007

JON W. DUDAS
*Director of the United States Patent and Trademark Office*